(12) United States Patent
Liu et al.

(10) Patent No.: US 9,528,420 B2
(45) Date of Patent: Dec. 27, 2016

(54) SYSTEM AND METHOD FOR CREATING CATALYST OBD LIMIT PARTS FOR EXHAUST AFTERTREATMENT APPLICATIONS

(71) Applicant: Cummins Emission Solutions, Inc., Columbus, IN (US)

(72) Inventors: Qiang Liu, Columbus, IN (US); Yi Liu, Columbus, IN (US); Zheng Liu, Knoxville, TN (US); Arvind V. Harinath, Columbus, IN (US); Huiling Li, Columbus, IN (US)

(73) Assignee: CUMMINS EMISSION SOLUTIONS, INC., Columbus, IN (US)

( * ) Notice: Subject to any disclaimer, the term of this patent is extended or adjusted under 35 U.S.C. 154(b) by 0 days.

(21) Appl. No.: 14/494,312

(22) Filed: Sep. 23, 2014

(65) Prior Publication Data

US 2016/0084136 A1    Mar. 24, 2016

(51) Int. Cl.

| | | |
|---|---|---|
| *F01N 11/00* | (2006.01) |
| *B01J 29/76* | (2006.01) |
| *B01J 37/02* | (2006.01) |
| *B01J 37/08* | (2006.01) |
| *B01J 35/04* | (2006.01) |
| *G01N 31/10* | (2006.01) |

(52) U.S. Cl.
CPC ............... *F01N 11/00* (2013.01); *B01J 29/76* (2013.01); *B01J 35/04* (2013.01); *B01J 37/0215* (2013.01); *B01J 37/08* (2013.01); *G01N 31/10* (2013.01); *F01N 2510/068* (2013.01); *F01N 2550/02* (2013.01)

(58) Field of Classification Search
CPC ........................ B01J 37/0215; B01J 37/0045
See application file for complete search history.

(56) References Cited

U.S. PATENT DOCUMENTS 7,033,969 B1 *  4/2006  Jobson ............... B01D 53/9418
                                                          502/64
2009/0081098 A1 * 3/2009 Golden ............. B01D 53/9418
                                                         423/239.2

* cited by examiner

*Primary Examiner* — Jill Warden
*Assistant Examiner* — Matthew Krcha
(74) *Attorney, Agent, or Firm* — Foley & Lardner LLP

(57) ABSTRACT

Catalyst diagnostic limit parts and methods for making catalyst diagnostic limit parts are disclosed. An exemplary catalyst diagnostic limit part includes a substrate and a washcoat coating the substrate. The washcoat includes an active catalyst and an inactive catalyst at a predetermined ratio of active catalyst to inactive catalyst so as to control the performance of the catalyst diagnostic limit part.

12 Claims, 4 Drawing Sheets

SYSTEM AND METHOD FOR CREATING CATALYST OBD LIMIT PARTS FOR EXHAUST AFTERTREATMENT APPLICATIONS

TECHNICAL FIELD

The present application relates generally to on-board diagnostics (OBD) limit parts for exhaust aftertreatment systems.

BACKGROUND

OBD systems are utilized to continuously monitor vehicle systems and components during vehicle operation for malfunctions and disturbances. Any errors or faults detected by the OBD system are stored in the system's memory, and errors and/or faults can be readily accessed by technicians and operators to facilitate troubleshooting and repairs.

Engine exhaust emissions regulations have become increasingly stringent over recent years. For example, for heavy-duty and medium-duty diesel vehicle applications, the California Air Resource Board (CARB) has mandated OBD monitoring and malfunction detection, with increasingly stringent OBD monitoring requirements scheduled to be phased in over time.

In various jurisdictions, regulations stipulate that all emission-related systems and components must be monitored to detect an increase in toxic exhaust gas emissions in the event of a malfunction. The regulations define malfunction criteria for various exhaust aftertreatment components, such as diesel oxidation catalysts (DOCs), selective catalytic reduction (SCR) catalysts, SCR on filter (SCRF), diesel particulate filters (DPFs), and other components. For example, certain regulations require that a detected malfunction be displayed to the operator via a malfunction indicator lamp (MIL) if a fault results in exhaust emissions exceeding certain thresholds (e.g., 2.0 times the applicable standards). For example, Table 1 below lists malfunction criteria specified by CARB's OBD II regulations for medium-duty diesel vehicles.

Catalysts (e.g., DOCs and SCR catalysts) may deteriorate over time due to several mechanisms. One example catalyst deterioration mechanism is thermal aging, which results from exposure to high exhaust gas temperatures over time. For example, thermal aging can result in sintering of noble metals, loss of oxygen storage capacity, and phase transformation of the washcoat. Thermal aging can reduce a catalyst's conversion efficiency to the point that the catalyst is determined to have malfunctioned. Emissions regulations, such as those listed in Table 1, specify malfunction criteria for detecting malfunctions of various components, such as catalysts.

SUMMARY

Various embodiments relate to catalyst diagnostic limit parts. An example catalyst diagnostic limit part includes a substrate and a washcoat coating the substrate. The washcoat includes an active catalyst and an inactive catalyst at a predetermined ratio of active catalyst to inactive catalyst so as to control the performance of the catalyst diagnostic limit part.

Various other embodiments relate to a method for preparing a catalyst diagnostic limit part. An example method includes preparing a washcoat slurry including an active catalyst and an inactive catalyst. The washcoat slurry includes a predetermined ratio of active catalyst to inactive catalyst so as to control the performance of the catalyst diagnostic limit part. The method also includes coating a substrate with the washcoat slurry.

Various other embodiments relate to an on-board diagnostic (OBD) limit test system. An example OBD limit test system includes an exhaust gas source. The OBD limit test system also includes a catalyst diagnostic limit part fluidly coupled to the exhaust gas source and configured to receive exhaust gas from the exhaust gas source. The catalyst diagnostic limit part includes a substrate and a washcoat coating the substrate. The washcoat includes an active catalyst and an inactive catalyst at a predetermined ratio of active catalyst to inactive catalyst so as to control the performance of the catalyst diagnostic limit part. The OBD limit test system also includes a plurality of exhaust gas sensors configured to measure operational parameters of the exhaust gas. Further yet, the OBD limit test system includes an OBD system operably coupled to the exhaust gas sensors. The OBD system is configured to detect a malfunction of the catalyst diagnostic limit part.

These and other features, together with the organization and manner of operation thereof, will become apparent from the following detailed description when taken in conjunction with the accompanying drawings.

TABLE 1

| California OBD II Malfunction Criteria: Engine certified Medium Duty Diesel Vehicles | | | | |
| --- | --- | --- | --- | --- |
| Monitor | Model Year | NMHC or CO | NOx | PM |
| NMHC catalyst, NOx conversion catalyst, NOx adsorber, PM filter | 2007-2009 | 2.5x | A.S. + 0.5 | 0.09 g/bhp-hr[b] |
| | 2010-2012 | 2.5x | A.S. + 0.3-0.4 | 0.07 g/bhp-hr |
| | 2013 and later | 2.0x | A.S. + 0.2 | 0.03 g/bhp-hr[c] |
| Upstream AFR sensor, VVT, fuel system monitor, downstream sensors, NOx and PM sensors, EGR system monitor, boost pressure monitor, cold start emission reduction strategy | Engines certified to NOx standard >0.50 g/bhp-hr | | | |
| | 2007 and later | 1.5-2.5x | 1.5-2.0x | 0.03-0.05 g/bhp-hr[c] |
| | Engines certified to NOx standard ≤0.50 g/bhp-hr | | | |
| | 2007-2012 | 2.5x | A.S. + 0.3-0.4 | 0.03-0.05 g/bhp-hr[c] |
| | 2013 and later | 2.0x | A.S. + 0.2 | 0.03 g/bhp-hr[c] |
| Misfire monitor | 2010 and later | 2.0x | 2.0x | 0.03 g/bhp-hr[c] |

A.S.—applicable standard, g/bhp-hr
[a] for 2007 through 2012 model years PM filter malfunction criteria may exclude detection of specific failure modes (e.g., combined failure of partially melted and partially cracked substrates) to prevent significant errors of commission
[b] for 2007 through 2009 vehicles certified to a PM emission standard of 0.08 g/bhp-hr or higher, a malfunction criteria of 1.5x the applicable PM standard applies
[c] A malfunction criteria of A.S. + 0.02 may also be used in place of 0.03 g/bhp-hr and A.S. + 0.04 in place of 0.05 g/bhp-hr

DETAILED DESCRIPTION

Figure 1A:
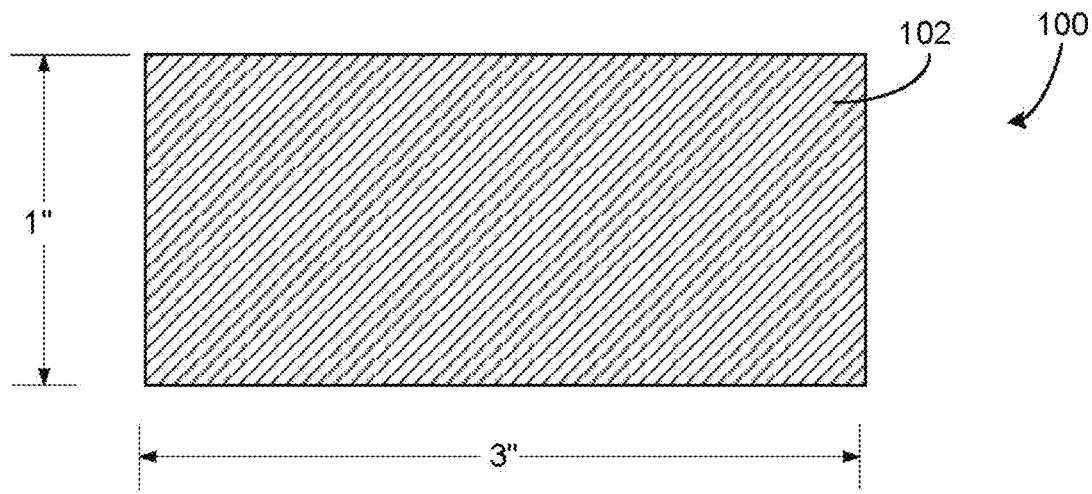
FIG. 1A illustrates a fully-coated DOC test sample in accordance with various embodiments.

In order to test OBD systems' ability to determine catalyst malfunction, original equipment manufacturers (OEMs) must provide "OBD limit parts." OBD limit parts simulate real-world catalyst deterioration under various engine operating conditions. Such OBD limit parts are used to calibrate and validate OBD catalyst monitoring systems to the required thresholds. For example, OBD limit parts are used to demonstrate detection of malfunctions at or near the applicable OBD thresholds.

OBD limit parts are conventionally produced using one of at least three methods: (1) the thermal aging method; (2) the slice method; and (3) the partially-coated method. The thermal aging method involves exposing a catalyst to elevated temperatures for extended periods of time to simulate real-world deterioration. However, the thermal aging method has several limitations. First, catalyst performance degradation is not linear with respect to thermal aging time or temperature. Hence, it is difficult to determine the proper combination of thermal aging time and temperature to achieve the desired performance degradation. Second, thermal aging may require a considerable amount of time. Third, the repeatability of thermal aging method is low, thereby causing high variability in test results.

Each of the slice method and the partially-coated method involves reducing the coated catalyst length. However, the slice method utilizes a smaller catalyst substrate that is fully coated, whereas the partially-coated method utilizes a full-size catalyst substrate that is partially coated (e.g., only a front section of the catalyst substrate is coated). Each of the slice method and the partially-coated method has several limitations. First, catalyst performance is not sensitive to space velocity (SV) until a very high SV or a very small coated catalyst length is used. SV refers to the quotient of the entering volumetric flow rate of the reactants divided by the reactor volume (e.g., the catalyst bed volume), which indicates how many reactor volumes of feed (e.g., exhaust gas) can be treated in a unit time. However, using a small catalyst slice (e.g., via the slice method) leads to difficulties in canning (e.g., installing the catalyst in a housing). Second, with a small coated catalyst length, catalyst performance becomes sensitive to the coated catalyst (e.g., catalyst brick) length variations. A small change in the coated catalyst length leads to large variation in performance. Therefore, catalyst performance is noisy and difficult to tune for OBD limit parts prepared using either of the slice method and the partially-coated method.

Various embodiments relate to improved OBD limit parts. More specifically, various embodiments relate to OBD limit parts using a particular amount of catalyst loading that is less than a conventionally-full amount, applied onto a full-length, fully-coated coated (non-sliced and non-partially-coated) substrate. For example, for DOC limit parts according to various embodiments, a particular amount of platinum group metal (PGM) loading that is less than a conventionally-full amount was applied onto a full-length, fully-coated substrate. In other examples according to various embodiments, for any of SCR catalysts, AMOx catalysts, and SCRF catalysts, a particular amount of active catalyst (e.g., Cu zeolite) loading that is less than a conventionally-full amount was applied onto a full-length, fully-coated coated substrate. For these examples and others, using a particular amount of catalyst loading that is less than a conventionally-full amount, applied onto a full-length, fully-coated (non-sliced and non-partially-coated) substrate was found to mimic real-world catalyst degradation due to aging and poisoning. Compared with conventional OBD limit parts (e.g., those created using the thermal aging method, the slice method, or the partially-coated method), OBD limit parts in accordance with various embodiments are more sensitive to performance, more controllable (e.g., tunable to particular catalyst performance levels), more measurable, and more realistic. OBD limit parts in accordance with various embodiments can include limit parts for various catalyst components, such as DOCs, combined DOCs and diesel particulate filters (DPFs), SCR catalysts, SCRF catalysts, and ammonia oxidation (AMOX) catalysts, among others. Thus, various embodiments enable precisely engineered OBD limit parts, which in turn enable precisely engineered OBD control.

The metals contemplated in PGMs include, in certain embodiments, any PGM. Additionally or alternatively, in certain embodiments a PGM includes only platinum, palladium, or rhodium. In certain embodiments, a PGM includes only platinum or palladium. In certain embodiments, a PGM includes only platinum. One of skill in the art, contemplating a particular system and catalyst, and having an understanding of the operating temperatures of the exhaust for the contemplated system, the aftertreatment components downstream of the catalyst, the desired reactions in the DOC, and the benefit of the disclosures herein, can readily determine the metals contemplated under PGM for a particular system.

The instant OBD limit parts have the same substrate size as conventional catalysts. Therefore, they are easy to can (e.g., install in a housing) using standard manufacturing processes. Further, the instant OBD limit parts utilize the same catalyst dry gain and the same binder to catalyst ratio as conventional catalysts to ensure consistent washcoat properties. According to various example embodiments, the substrate is one of a flow-through and a wall-flow substrate. A significant difference between the instant OBD limit parts and conventional OBD limit parts is the ratio of active catalyst to inactive catalyst in the washcoat, which is referred to herein as the active/inactive catalyst ratio. By changing the active/inactive catalyst ratio, the catalyst performance can be precisely tuned to the desired target and thus can be engineered to precisely trigger the OBD malfunction threshold.

Inactive catalysts are produced in various ways. In some examples, inactive catalysts are produced by thermally aging an active catalyst until it becomes inactive. In some examples, inactive catalysts are produced by using particular materials that are inert to certain chemical reactions (e.g., un-exchanged zeolites or other chemically-inert materials) to simulate inactive Cu-exchange zeolites.

Test samples of the instant OBD limit parts were analyzed against test samples from conventional OBD limit parts produced using the partially-coated method to evaluate the efficacy of the instant OBD limit parts. In particular, DOC substrates were utilized for first and second tests. As shown in Table 2 below, six groups each of fully-coated and partially-coated DOC substrates were analyzed. Each of the six sample groups have different levels of PGM loading. The performance of the DOC substrate coating test samples was analyzed in terms of $NO_x$ conversion and CO/HC light-off.

TABLE 2

DOC Substrate Coating Matrix

| Coating Method | PGM Loading (g/ft³) Sample Group | | | | | |
|---|---|---|---|---|---|---|
| | 1 | 2 | 3 | 4 | 5 | 6 |
| Fully-Coated (1 in. × 3 in.) | 1 | 2.5 | 5 | 10 | 20 | 40 |
| Partially-Coated (first 1 in. of 1 in. × 3 in.) | 3 | 7.5 | 15 | 30 | 60 | 120 |

Figure 1B:
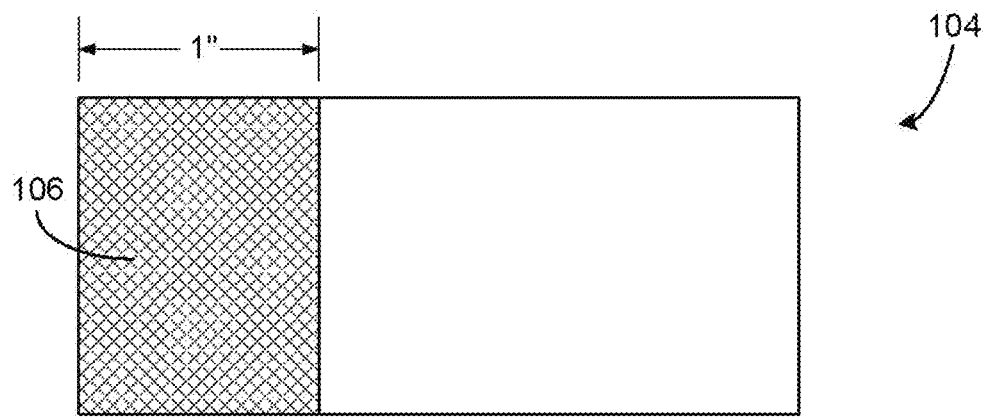
FIG. 1B illustrates a partially-coated DOC test sample.

FIGS. 1A and 1B illustrate test samples that were used for the DOC substrate coating test. As shown in FIGS. 1A and 1B, each of the test samples include degreened 1 in.×3 in. pilot core samples taken from each sample substrate. In particular, FIG. 1A illustrates a fully-coated test sample 100 in accordance with the instant OBD limit parts. The fully-coated test sample 100 has a first coating 102 that extends across the entire length of the fully-coated test sample 100. FIG. 1B illustrates a partially-coated substrate test sample 104 in accordance with conventional OBD limit parts. The partially-coated sample 104 has a second coating 106 that extends across the first 1 in. of the 1 in.×3 in. partially-coated sample 104. The first coating 102 has an active/inactive catalyst ratio of 1:2. In other words, for every one unit volume of active catalyst included in the first coating 102, two unit volumes of inactive catalyst are included. Therefore, because the first coating 102 is three-times larger in area than the second coating 106, the first and second coatings 102, 106 have the same total PGM loading.

Figure 2A:
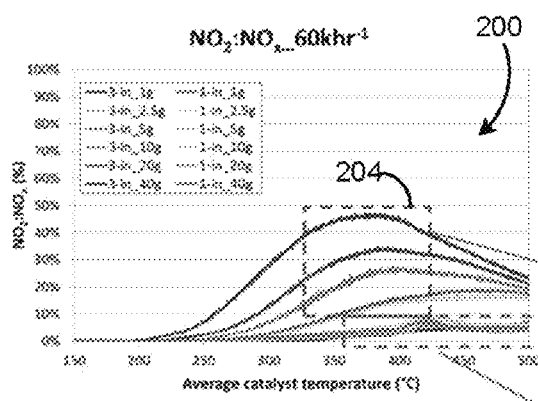
FIG. 2A is a plot of $NO_x$ conversion results of a first DOC substrate coating test conducted using a space velocity of 60 $khr^{-1}$.
Figure 2B:
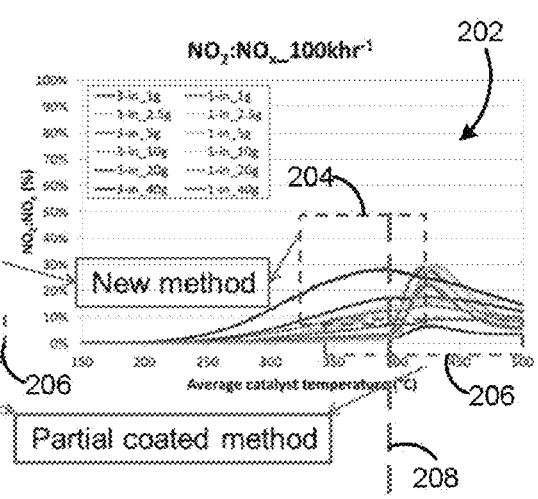
FIG. 2B is a plot of $NO_x$ conversion results of a second DOC substrate coating test conducted using a space velocity of 100 $khr^{-1}$.

FIGS. 2A and 2B illustrate $NO_x$ conversion (e.g., which may alternatively be described in terms of NO oxidation) results of the DOC substrate coating test. In particular, FIG. 2A illustrates first test results 200 of a first test conducted using an SV of 60 khr$^{-1}$ and FIG. 2B illustrates second test results 202 of a second test conducted using an SV of 100 khr$^{-1}$. Each of the first and second test results 200, 204 include a first grouping 204 of test results corresponding to the fully-coated samples 100 in accordance with the instant OBD limit parts, and a second grouping 206 of test results corresponding to the partially-coated samples 104 in accordance with conventional OBD limit parts.

The first and second test results 200, 202 clearly show that for the first grouping 204 corresponding to the fully-coated samples 100, the $NO_x$ conversion rate is highly sensitive to PGM loading, whereas for the second grouping 206 corresponding to the partially-coated samples 104, the $NO_x$ conversion rate shows very little sensitivity to PGM loading. Despite the PGM loading variance from 3 to 120 g/ft³, the second grouping 206 corresponding to the partially-coated samples 104 exhibits negligible $NO_x$ conversion below 400° C. Thus, the instant OBD limit parts provide much higher $NO_x$ conversion rate sensitivity to PGM loading than the conventional OBD limit parts. Therefore, the instant OBD limit parts enable improved simulation predictability, which in turn enables precisely engineered OBD control.

As shown in FIG. 2B, $NO_x$ conversion rises quickly above approximately 400° C. for the second grouping 206 corresponding to the partially-coated samples 104. To understand the mechanism driving this behavior, $NO_x$ conversion versus HD lightoff was analyzed for the second test 202.

Figure 2D:
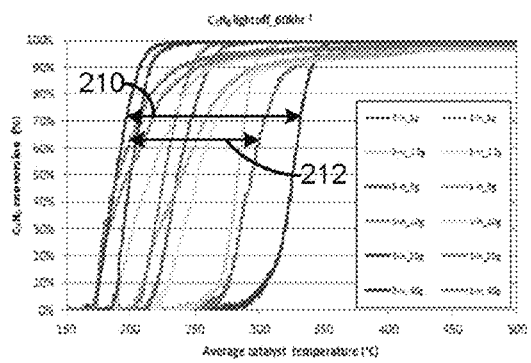
FIG. 2D is a plot of $NO_x$ conversion versus hydrocarbon lightoff for the first test of FIG. 2A.
Figure 2C:
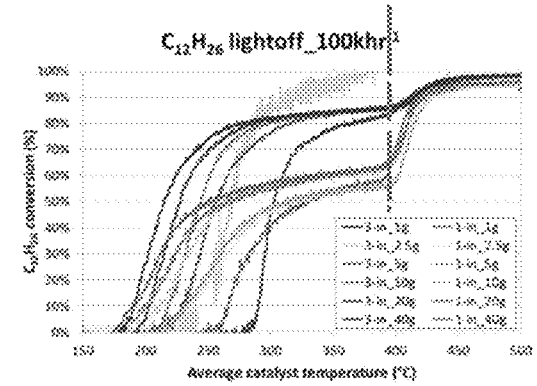
FIG. 2C is a plot of $NO_x$ conversion versus hydrocarbon lightoff for the second test of FIG. 2B.

FIG. 2C illustrates $NO_x$ conversion versus hydrocarbon (HC) lightoff for the second test 202 conducted using an SV of 100 khr$^{-1}$. As shown in FIG. 2C, the onset temperature 208 at which each of $NO_x$ conversion (FIG. 2B) and HC lightoff (FIG. 2C) takes place is approximately 400° C. This indicates that at lower temperatures, long chain hydrocarbons (e.g., dodecane) compete with $NO_x$ conversion, thereby significantly inhibiting the $NO_x$ conversion. Such inhibition is so strong that even at 120 g/ft³ of PGM loading, the $NO_x$ conversion efficiency is relatively low below 400° C. Until the temperature reaches 400° C., at which point dodecane begins to be fully oxidized, the $NO_x$ conversion efficiency begins to improve. The fully-coated samples 100 of the first grouping 204 have a larger area than the partially-coated samples 104 of the second grouping 206 to accommodate $NO_x$ conversion. Therefore, the $NO_x$ conversion rate of the fully-coated samples 100 of the first grouping 204 is not inhibited by long chain hydrocarbons, which, as shown with the partially-coated samples 104 of the second grouping 206, can mask $NO_x$ conversion efficiency. Production parts utilize fully-coated substrates. Therefore, the fully-coated samples 100 of the first grouping 204 more closely simulate the production parts than the partially-coated samples 104 of the second grouping 206. In fact, as shown in FIGS. 2B and 2C, utilizing partially-coated samples can significantly skew $NO_x$ conversion test data.

FIG. 2D illustrates $NO_x$ conversion versus hydrocarbon (HC) lightoff for the first test 200 conducted using an SV of 60 khr$^{-1}$. As shown in FIG. 2D, a first differential 210 between the maximum and minimum PGM loading levels of the fully-coated samples 100 of the first grouping 204 is larger than a second differential 212 between the maximum and minimum PGM loading levels of the partially-coated samples 104 of the second grouping 206. Therefore, the fully-coated samples 100 of the first grouping 204 exhibit more significant HC lightoff boundaries according to PGM loading as compared to the partially-coated samples 104 of the second grouping 206, which is preferential for OBD limit testing.

In addition to DOC test samples, SCR catalyst test samples of the instant OBD limit parts were analyzed against test samples from conventional OBD limit parts produced using the slice method to evaluate the efficacy of the instant OBD limit parts. As shown in Tables 3 and 4 below, six groups each of fully-coated and partially-coated SCR catalyst substrates were analyzed. Each of the six sample groups has different levels of active catalyst (e.g., Cu zeolite) loading. As shown in Table 3, active catalyst loading for the instant SCR catalyst OBD limit parts was set by varying the active/inactive SCR catalyst ratio on fully-coated substrates. As shown in Table 4, active catalyst loading for the conventional SCR catalyst OBD limit parts was controlled by varying the length of the substrate via the slice method. The SCR catalyst test was conducted utilizing a gas species comprising 200 ppm $NO_R$, 200 ppm $NH_3$, and 10% $O_2$, with an SV of 60 $khr^{-1}$.

TABLE 3

Instant SCR Catalyst OBD Limit Parts

| Sample | Dry Gain | CPSI | Active SCR | Inactive SCR | Binder | Diameter | Length | SCR Amount |
|---|---|---|---|---|---|---|---|---|
| Baseline | 2.5 g/in³ | 600/3 | 100% | 0% | 100% | 10.5 in. | 11 in. | 100% |
| A1 | 2.5 g/in³ | 600/3 | 75% | 25% | 100% | 10.5 in. | 11 in. | 75% |
| A2 | 2.5 g/in³ | 600/3 | 50% | 50% | 100% | 10.5 in. | 11 in. | 50% |
| A3 | 2.5 g/in³ | 600/3 | 25% | 75% | 100% | 10.5 in. | 11 in. | 25% |
| A4 | 2.5 g/in³ | 600/3 | 10% | 90% | 100% | 10.5 in. | 11 in. | 10% |
| A5 | 2.5 g/in³ | 600/3 | 5% | 95% | 100% | 10.5 in. | 11 in. | 5% |

TABLE 4

Conventional SCR Catalyst OBD Limit Parts (Slice Method)

| Sample | Dry Gain | CPSI | Active SCR | Inactive SCR | Binder | Diameter | Length | SCR Amount |
|---|---|---|---|---|---|---|---|---|
| Baseline | 2.5 g/in³ | 600/3 | 100% | 0% | 100% | 10.5 in. | 11 in. | 100% |
| B1 | 2.5 g/in³ | 600/3 | 100% | 0% | 100% | 10.5 in. | 8.25 in. | 75% |
| B2 | 2.5 g/in³ | 600/3 | 100% | 0% | 100% | 10.5 in. | 5.5 in. | 50% |
| B3 | 2.5 g/in³ | 600/3 | 100% | 0% | 100% | 10.5 in. | 2.75 in. | 25% |
| B4 | 2.5 g/in³ | 600/3 | 100% | 0% | 100% | 10.5 in. | 1.1 in. | 10% |
| B5 | 2.5 g/in³ | 600/3 | 100% | 0% | 100% | 10.5 in. | 0.55 in. | 5% |

Figure 3A:
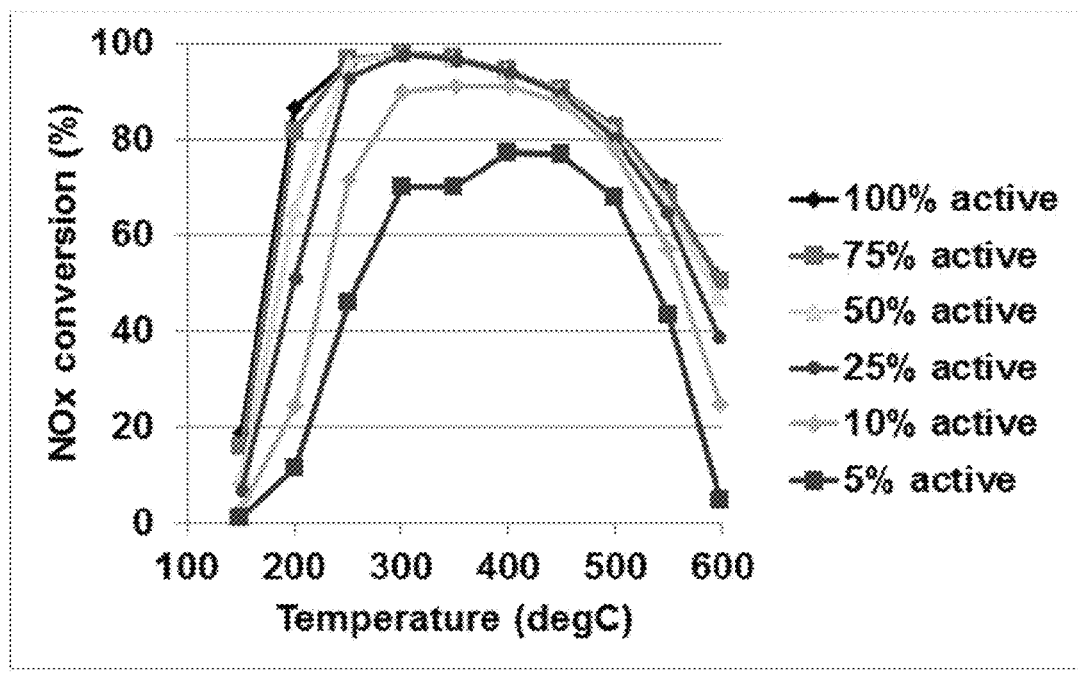
FIG. 3A is a plot of $NO_x$ conversion results for fully-coated SCR catalyst OBD limit parts with various active/inactive catalyst ratios, in accordance with various embodiments.
Figure 3B:
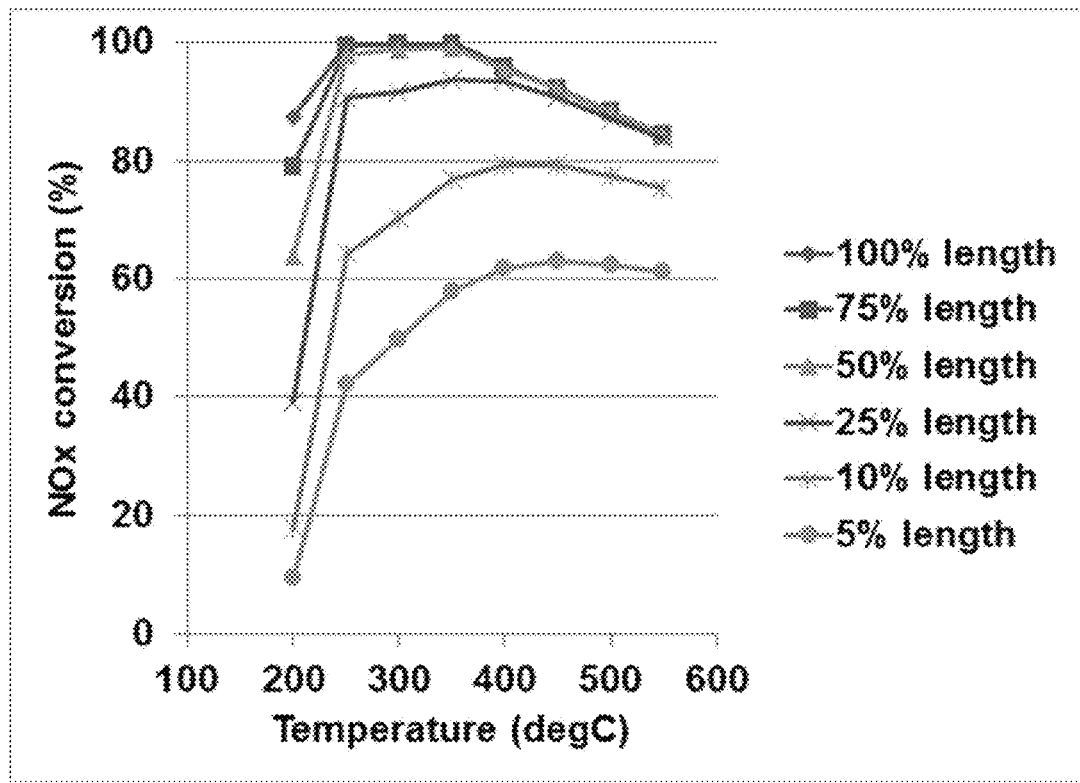
FIG. 3B is a plot of $NO_x$ conversion results for partially-coated SCR catalyst OBD limit parts prepared using the slice method at various lengths.

FIG. 3A illustrates $NO_x$ conversion results for the instant SCR catalyst OBD limit parts prepared using the fully-coated method with various active/inactive catalyst ratios. FIG. 3B illustrates $NO_x$ conversion results for the conventional SCR catalyst OBD limit parts prepared using the slice method at various lengths.

As shown in FIGS. 3A and 3B, an OBD threshold of 60% $NO_x$ conversion at 200° C. can be achieved utilizing the instant SCR catalyst OBD limit parts utilizing a 25%:75% active/inactive catalyst ratio, or with the conventional SCR catalyst OBD limit parts utilizing an SCR catalyst substrate length of 2.75 in. via the slice method. Considering these results, the instant SCR catalyst OBD limit parts prepared using the fully-coated method with various active/inactive catalyst ratios as described herein include a number of benefits.

First, the instant OBD limit parts are easy to can (e.g., install in a housing). The instant OBD limit parts have a catalyst substrate length of 11 in., while the conventional OBD limit parts utilizing the slice method have a catalyst substrate length of only 2.75 in. In this case, the conventional OBD limit parts have a length/diameter ratio of 0.26, which is smaller than Applicant's packaging requirement of a length/diameter ratio of at least 0.33.

Second, the instant OBD limit parts have a higher capability to tune performance. With the instant OBD limit parts, catalyst conversion can be brought down by further reducing the active/inactive catalyst ratio. However, with the conventional OBD limit parts prepared using the slice method, a further reduction in catalyst conversion requires a more aggressive reduction in catalyst length. Cutting the catalyst below 2.75 in. with high accuracy is technical challenging. Further, such a catalyst is difficult, if not impossible, to package.

Third, the instant OBD limit parts can be produced in a highly repeatable and consistent manner. The instant OBD limit parts can be consistently reproduced by washcoating the substrate of each with a washcoat slurry having a 25%:75% active/inactive catalyst ratio. On the other hand, consistently cutting catalyst substrate slices of 2.75 in. or even smaller is difficult. Accordingly, expected part-to-part variation of the slice method causes corresponding variations in OBD limit test results.

Finally, the impact of mass transfer on test results is eliminated by utilizing the instant OBD limit parts. Each of the instant OBD limit parts has the same substrate size and washcoat properties as production parts. However, the reduced substrate length of the conventional OBD limit parts prepared using the slice method leads to variability in the OBD test results due to variable mass transfer conditions.

Thus, the instant OBD limit parts constructed according to various embodiments have several significant advantages over conventional OBD limit parts, including (1) highly repeatable OBD limit part production; (2) easily tunable performance by varying the active/inactive catalyst ratio; (3) identical mass transfer properties as production parts; and (4) common packaging as production parts. Hence, the instant OBD limit parts are desirable over conventional OBD limit parts because they result in minimal noise or variation in OBD test results.

Figure 4:
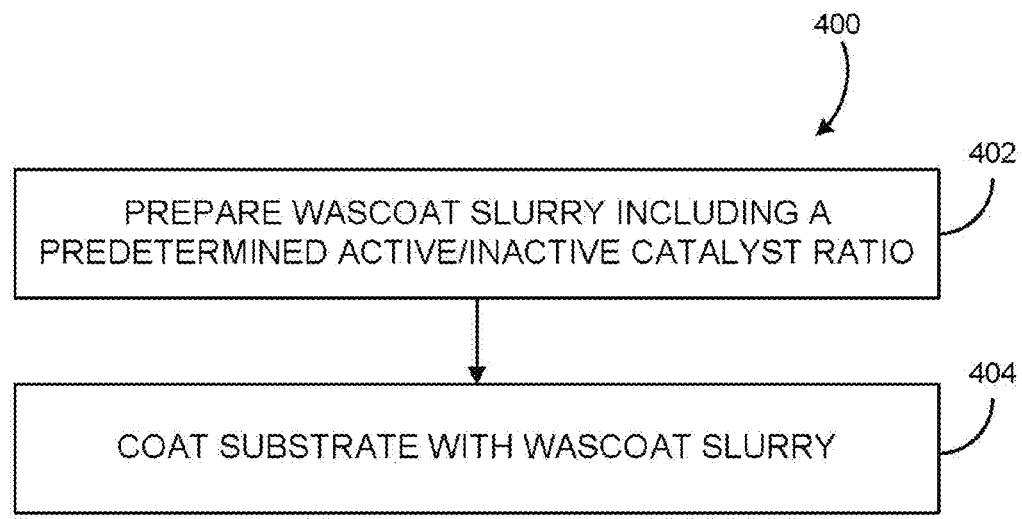
FIG. 4 is a flow diagram illustrating a method of preparing OBD limit parts.

FIG. 4 is a flow diagram illustrating a method 400 of preparing OBD limit parts, according to an example embodiment. For example, the method 400 can be used to prepare the OBD limit part 100 of FIG. 1. According to various example embodiments, the method 400 can be used to prepare DOC limit parts, SCR catalyst limit parts, AMOX limit parts, among other types of limit parts.

At 402, a washcoat slurry including an active catalyst and an inactive catalyst is prepared. The washcoat slurry includes a predetermined ratio of active catalyst to inactive catalyst so as to control the performance of the OBD limit part. For example, as described above in connection with FIGS. 3A and 3B, an OBD threshold of 60% $NO_x$ conversion was achieved utilizing instant SCR catalyst OBD limit parts utilizing a washcoat slurry having a 25%:75% active/inactive catalyst ratio. However, according to various example embodiments, the washcoat slurry can be prepared using any active/inactive catalyst ratio to produce a desired OBD threshold $NO_x$ conversion level.

At 404, a substrate is coated with the washcoat slurry. The substrate is fully-coated by the washcoat slurry. In some examples, the substrate has a length to diameter ratio of at least 0.33. OBD limit parts prepared using the method 400 of FIG. 4 provide numerous advantages over conventional OBD limit parts, which are discussed in detail above.

Figure 5:
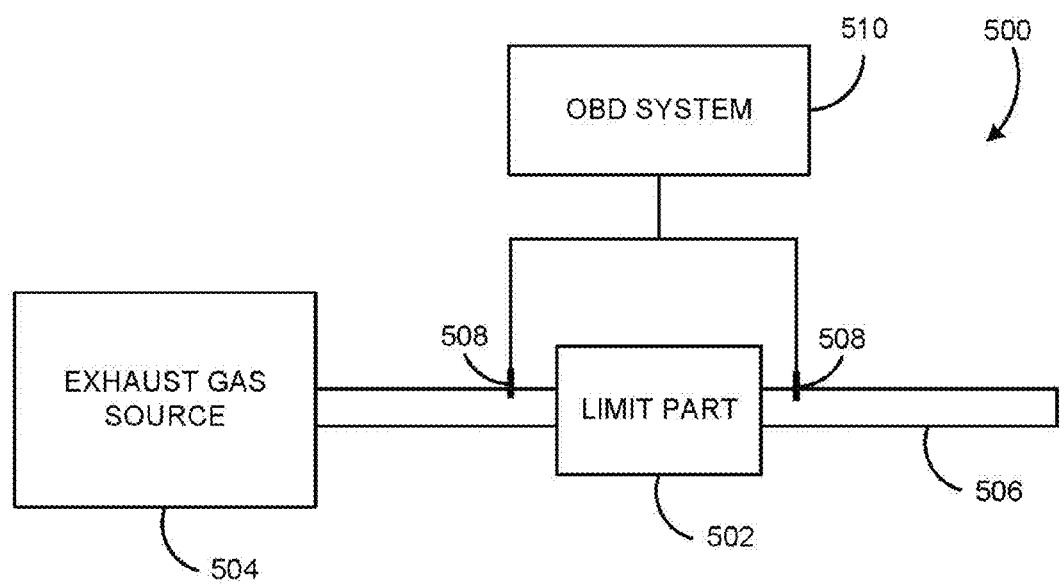
FIG. 5 is a block diagram of an exemplary OBD limit test system.

FIG. 5 is a block diagram of an OBD limit test system 500. The OBD limit test system 500 can be used to test an OBD limit part 502. According to example embodiments, the OBD limit part 502 (e.g., a catalyst diagnostic limit part) can be the same as or similar to the OBD limit part 100 of FIG. 1. The OBD limit test system 500 includes an exhaust gas source 504. In some embodiments, the OBD limit test system 500 is stationary (e.g., in a test laboratory or test cell). In such embodiments, the exhaust gas source 504 may include, for example, a vehicle on a chassis dynamometer, an engine on an engine dynamometer, or a synthetic exhaust gas source. In other embodiments, the OBD limit test system 500 is mobile. In such examples, the exhaust gas source 504 may include, for example, a vehicle operating on a road or on a test track.

The OBD limit part 502 is fluidly coupled to the exhaust gas source 504 via an exhaust passage 506. The OBD limit part 502 is configured to receive exhaust gas from the exhaust gas source 504 via the exhaust passage 506. The OBD limit part 502 includes a substrate and a washcoat coating the substrate. The washcoat includes an active catalyst and an inactive catalyst at a predetermined active/inactive catalyst ratio so as to control the performance of the OBD limit part. In one embodiment, the predetermined ratio is no higher than 30%:70%. In another embodiment, the predetermined ratio is no higher than 25%:75%. In further embodiments, the substrate has a length to diameter ratio of at least 0.33. Further yet, in some embodiments, the substrate is fully coated by the washcoat.

The OBD limit test system 500 also includes a plurality of exhaust gas sensors 508. The exhaust gas sensors 508 are configured to measure operational parameters of the exhaust gas flowing through the exhaust passage 506. According to various example embodiments, the OBD limit test system 500 includes more or fewer exhaust gas sensors 508 than shown in FIG. 5. Further, according to various example embodiments, the exhaust gas sensors 508 are be positioned differently than shown in FIG. 5. The exhaust gas sensors 508 may include, for example, temperature sensors, $NO_x$ sensors, nitrogen sensors, oxygen sensors (e.g., lambda sensors), pressure sensors, etc.

The OBD limit test system 500 also includes an OBD system 510 (e.g., an OBD-II system) operably coupled to the exhaust gas sensors 508. The OBD system 510 is configured to detect a malfunction of the OBD limit part 502. According to an example embodiment, the OBD system 510 includes data acquisition and analysis functionality, and memory to analyze signals received from the exhaust gas sensors 508 to detect a malfunction of the OBD limit part 502.

It should be noted that the terms "example" and "exemplary" as used herein to describe various embodiments are intended to indicate that such embodiments are possible examples, representations, and/or illustrations of possible embodiments (and such terms are not intended to connote that such embodiments are necessarily extraordinary or superlative examples).

While various embodiments of the disclosure have been shown and described, it is understood that these embodiments are not limited thereto. The embodiments may be changed, modified and further applied by those skilled in the art. Therefore, these embodiments are not limited to the detail shown and described previously, but also include all such changes and modifications.

What is claimed is:

1. A method comprising:
   identifying a predetermined amount of degradation of a catalyst to simulate by a catalyst diagnostic limit part;
   preparing a washcoat slurry including a first amount of an active catalyst and a second amount of an inactive catalyst at a predetermined ratio of the first amount to the second amount so as to simulate the predetermined amount of degradation of the catalyst;
   coating a substrate with the washcoat slurry; and
   installing the coated substrate in a housing to form the catalyst diagnostic limit part;
   wherein the predetermined ratio is no higher than 30%:70%.

2. The method of claim 1, wherein the predetermined ratio is no higher than 25%:75%.

3. The method of claim 1, further comprising thermally aging an active catalyst to produce the inactive catalyst.

4. The method of claim 1, wherein the inactive catalyst includes a chemically-inert material.

5. The method of claim 4, wherein the chemically-inert material includes un-exchanged zeolites.

6. The method of claim 1, wherein the substrate has a length to diameter ratio of at least 0.33.

7. The method of claim 1, wherein the substrate is fully coated by the washcoat slurry.

8. The method of claim 1, wherein the catalyst diagnostic limit part is a diesel oxidation catalyst.

9. The method of claim 1, wherein the catalyst diagnostic limit part is one of a selective catalytic reduction catalyst, a selective catalytic reduction catalyst on filter, and an ammonia oxidation catalyst.

10. The method of claim 1, wherein the catalyst diagnostic limit part includes each of a diesel oxidation catalyst and a diesel particulate filter.

11. The method of claim 1, wherein the substrate is a flow-through substrate.

12. The method of claim 1, wherein the substrate is a wall-flow substrate.

* * * * *